(12) United States Patent
Tanoguchi

(10) Patent No.: US 10,065,784 B2
(45) Date of Patent: Sep. 4, 2018

(54) PACKAGED MEDICINE-FILLED CONTAINER

(71) Applicant: TERUMO KABUSHIKI KAISHA, Tokyo (JP)

(72) Inventor: Kenji Tanoguchi, Fuji (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/273,251

(22) Filed: Sep. 22, 2016

(65) Prior Publication Data

US 2017/0008686 A1 Jan. 12, 2017

Related U.S. Application Data

(63) Continuation of application No. PCT/JP2015/059804, filed on Mar. 27, 2015.

(30) Foreign Application Priority Data

Mar. 28, 2014 (JP) .................................. 2014-070569

(51) Int. Cl.
*B65D 81/26* (2006.01)
*A61J 1/10* (2006.01)
(Continued)

(52) U.S. Cl.
CPC .............. *B65D 81/266* (2013.01); *A61J 1/10* (2013.01); *A61J 1/1468* (2015.05); *A61J 1/16* (2013.01);
(Continued)

(58) Field of Classification Search
CPC ................ B65D 81/206; B65D 75/326; B65D 2575/329; A61M 5/002; A61J 1/10;
(Continued)

(56) References Cited

U.S. PATENT DOCUMENTS 4,853,266 A * 8/1989 Cullen .................... B65D 65/46
206/204
4,872,553 A * 10/1989 Suzuki .................. A61J 1/1462
206/438
(Continued)

FOREIGN PATENT DOCUMENTS

| JP | 2000-050850 A | 2/2000 |
| JP | 2000-175989 A | 6/2000 |

(Continued)

OTHER PUBLICATIONS

International Search Report issued in International Patent Application No. PCT/JP2015/059804 dated Jun. 23, 2015 (with English-language translation).
(Continued)

*Primary Examiner* — Luan K Bui
(74) *Attorney, Agent, or Firm* — Foley & Lardner LLP

(57) ABSTRACT

A packaged medicine-filled container has a resin-made medicine-filled container in which a medicine is housed, a sealed packaging body in which the medicine-filled container is housed, and an oxygen scavenger housed inside the packaging body. The packaging body is hardly oxygen-permeable. Both a moisture-dependent type oxygen scavenger and a self-reacting type oxygen scavenger are used as the oxygen scavenger.

7 Claims, 5 Drawing Sheets

(51) Int. Cl.
*A61J 1/16* (2006.01)
*B65D 75/32* (2006.01)
*A61M 5/00* (2006.01)
*A61M 5/50* (2006.01)
*B01D 53/04* (2006.01)
*A61J 1/05* (2006.01)
*A61J 1/14* (2006.01)

(52) U.S. Cl.
CPC .......... *A61M 5/002* (2013.01); *A61M 5/5086* (2013.01); *B01D 53/04* (2013.01); *B65D 75/326* (2013.01); *A61J 1/05* (2013.01); *A61J 1/1406* (2013.01); *B01D 2253/112* (2013.01); *B01D 2257/104* (2013.01); *B01D 2259/4533* (2013.01); *B65D 2575/329* (2013.01)

(58) Field of Classification Search
CPC . A61J 1/1468; B01D 53/04; B01D 2253/112; B01D 2257/104; B01D 2259/4533
USPC .......... 206/204, 363, 364, 438, 571
See application file for complete search history.

(56) References Cited

U.S. PATENT DOCUMENTS

| | | | | |
|---|---|---|---|---|
| 4,936,314 A * | 6/1990 | Kasai | .............. | A61B 5/15003 206/438 |
| 4,998,400 A | 3/1991 | Suzuki et al. | | |
| 6,073,759 A * | 6/2000 | Lamborne | ............ | A61M 5/002 206/213.1 |
| 6,688,468 B2 * | 2/2004 | Waterman | ................ | A61J 1/00 206/524.1 |
| 7,708,719 B2 * | 5/2010 | Wilmot | .................. | A61J 1/062 206/364 |
| 2001/0048096 A1 | 12/2001 | Sakamoto et al. | | |
| 2003/0034264 A1 * | 2/2003 | Hamai | ..................... | A61L 2/04 206/364 |
| 2010/0174268 A1 | 7/2010 | Wilmot et al. | | |
| 2013/0081960 A1 * | 4/2013 | Schott | ................... | A61B 5/151 206/210 |
| 2013/0081974 A1 | 4/2013 | Hilliard et al. | | |
| 2014/0262883 A1 * | 9/2014 | Devouassoux | ....... | A61M 5/002 206/364 |
| 2015/0114855 A1 * | 4/2015 | Glick | ................... | A61F 2/1691 206/204 |

FOREIGN PATENT DOCUMENTS

| | | |
|---|---|---|
| JP | 2004-275616 A | 10/2004 |
| JP | 2006-016053 A | 1/2006 |
| JP | 2006-025874 A | 2/2006 |
| JP | 2006-096394 A | 4/2006 |
| JP | 2012-120585 A | 6/2012 |

OTHER PUBLICATIONS

English-language translation of International Preliminary Report on Patentability issued in International Patent Application No. PCT/JP2015/059804 dated Oct. 4, 2016.

Extended European Search Report from corresponding application 15768405.1 dated Sep. 26, 2017.

* cited by examiner

PACKAGED MEDICINE-FILLED CONTAINER

CROSS-REFERENCE TO RELATED APPLICATIONS

This application is a continuation of PCT Application No. PCT/JP2015/059804, filed on Mar. 27, 2015, which claims priority to Japanese Patent Application No. 2014-070569, filed on Mar. 28, 2014, the entireties of which are hereby incorporated by reference.

TECHNICAL FIELD

The present invention relates to a packaged medicine-filled container in which an oxygen scavenger is housed.

BACKGROUND ART

A resin-made medicine-filled container body housing a medicine in a resin-made container thereof such as a prefilled syringe, an ample, and the like is used. To stabilize the medicine filled inside the container body, the medicine-filled container housed inside a sealed packaging body is also used. According to the disclosure made in Japanese Patent Application Laid-Open Publication No. 2006-16053 (patent document 1), to stabilize the medicine, the oxygen scavenger is housed inside the packaging body of the packaged medicine-filled container body.

PRIOR ART DOCUMENTS

Patent Documents

Patent document 1: Japanese Patent Application Laid-Open Publication No. 2006-16053

SUMMARY OF THE INVENTION

Problems to be Solved by the Invention

In the packaged medicine-filled container disclosed in the patent document 1, the packaging body having the tray-shaped container body and the sheet-shaped sealing member for openably sealing the opening of the container body is used. The use of the packaging body having this form is preferable in that the prefilled syringe housed inside the packaging body is protected from shocks and the like. As disclosed in the patent document 1, by housing the oxygen scavenger inside the packaging body, it is possible to stabilize the medicine.

As a result of the investigations conducted by the present inventors, they found that to stabilize the medicine more reliably, it is preferable to remove oxygen from the inside of the packaging body as quickly as possible in an early period of time and that it is desirable to remove the oxygen continuously after the packaging body goes into a low-oxygen state.

Therefore it is an object of the present invention to provide a packaged medicine-filled container including a resin-made medicine-filled container in which a medicine is housed and a sealed packaging body in which the medicine-filled container is housed, wherein oxygen is quickly removed in an early period of time and continuously removed after the oxygen in the early period of time is removed.

Means for Solving the Problems

The means for achieving the above-described object has a form as described below.

A packaged medicine-filled container of the present invention includes a resin-made medicine-filled container in which a medicine is housed and a sealed packaging body in which the medicine-filled container is housed. The packaged medicine-filled container has an oxygen scavenger housed inside the packaging body. The packaging body is hardly oxygen-permeable. Both a moisture-dependent type oxygen scavenger and a self-reacting type oxygen scavenger are used as the oxygen scavenger.

MODE FOR CARRYING OUT THE INVENTION

Figure 1:
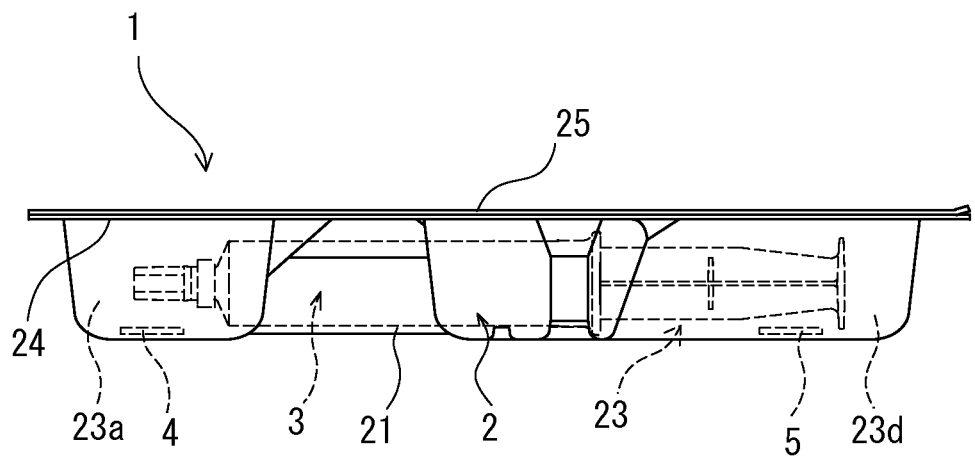
FIG. 1 is a front view of a packaged medicine-filled container which is one embodiment of the present invention.

A packaged medicine-filled container of the present invention is described below with reference to embodiments shown in the drawings.

A packaged medicine-filled container 1 of the present invention is constructed of a resin-made medicine-filled container 3 in which a medicine 39 is housed and a sealed packaging body 2 in which the medicine-filled container 3 is housed. The packaged medicine-filled container 1 has an oxygen scavenger housed inside the packaging body 2. The packaging body 2 is hardly oxygen-permeable. As the oxygen scavenger, both a moisture-dependent type oxygen scavenger 4 and a self-reacting type oxygen scavenger 5 are used.

In the packaged medicine-filled container 1 of this embodiment, as the medicine-filled container 3, a prefilled syringe in which a liquid medicine is filled as the medicine 39 is used.

The packaging body 2 to be used in this embodiment has a tray 21 for housing the prefilled syringe which is the medicine-filled container 3 and a sealing member 25 for openably sealing an opening 22 of the tray 21.

In the embodiment shown in FIGS. 1 through 4, the packaging body 2 has the tray 21 having a container body housing part 23 for housing the resin-made medicine-filled container 3 and the peelable sealing sheet (sealing member)

25 for sealing a concave opening 22. The packaging body 2 of the embodiment shown in FIG. 1 is a blister packaging body. The packaging body 2 of this embodiment of the present invention has a configuration capable of housing the prefilled syringe which is one example of the medicine-filled container 3 and is described later.

Specifically, the tray 21 has the container body housing part 23 and a flange-formed part 24 formed around the container body housing part 23. The container body housing part 23 has a housing portion 23a for housing a front end portion of an outer cylinder 31 without substantially contacting the vicinity of an injection needle mounting portion of the outer cylinder 31, a housing and holding portion 23b, for housing and holding an intermediate portion of the outer cylinder 31, which contacts an outer peripheral surface of the intermediate portion of the outer cylinder 31 and houses the intermediate portion thereof in such a way as to prevent a movement of the outer cylinder in a horizontal lateral direction, a portion 23c for housing a flange-formed part of the outer cylinder 31, and a plunger housing portion 23d for housing a plunger part 35.

It is preferable that materials for the tray 21 are hardly oxygen-permeable and have a certain degree of strength and hardness. It is preferable that the tray 21 has a base material layer consisting of polyolefin such as polypropylene and polyethylene, vinyl chloride resin, polyester resin or polystyrene/polypropylene resin and a layer, consisting of hardly oxygen-permeable resin (for example, polyvinylidene chloride, ethylene-vinyl alcohol copolymer, polyethylene terephthalate), which is disposed on an upper surface of the base material layer or on a lower surface thereof and has a thickness of 30 to 70 µm. More specifically, it is preferable that the tray consists of three layers of polyethylene terephthalate/ethylene-vinyl alcohol copolymer/polypropylene.

The sealing sheet (sealing member) 25 is airtightly fixed to an upper surface of the tray 21 in such a way as to seal a prefilled syringe housing concave portion therewith. It is preferable that the sealing sheet 25 is formed of a hardly oxygen-permeable film, an adhesive resin layer fixed to at least an outer peripheral portion of a lower surface of the hardly oxygen-permeable film, and a surface protection layer formed on an upper surface of the hardly oxygen-permeable film. The hardly oxygen-permeable film suppresses the permeation of oxygen into the tray from the outside. As the hardly oxygen-permeable film, it is possible to preferably use a metal foil such as an aluminum foil, a silver film or a gold foil; a film on which a metal such as aluminum, silver or gold has been deposited; a film on which an inorganic substance such as SiOX has been deposited; and a hardly oxygen-permeable resin film, for example, a film made of polyvinylidene chloride, polyvinylidene chloride-polyvinyl chloride, polyvinylidene chloride-acrylic acid ester copolymer, and high-density polyethylene.

The adhesive resin layer has a function of peelably heat-sealing the hardly oxygen-permeable film and the tray 21 to each other. The following various easily peelable mechanisms can be utilized. For example, in a case where polypropylene is used to form a heat sealing surface of the tray 21, it is possible to preferably use olefin resin such as ethylene-vinyl acetate resin, ethylene-acrylic acid resin, a mixture of polypropylene and polyethylene, and an adhesive agent consisting of two-liquid curing type urethane based dry laminate. In a case where polyvinyl chloride is used to form the tray 21, as the adhesive resin layer, it is possible to preferably use the olefin resin such as the ethylene-vinyl acetate resin and the ethylene-acrylic acid resin, a mixture of polystyrene and a styrene-butadiene block copolymer, and a vinyl chloride-vinyl acetate copolymer, and the adhesive agent consisting of the two-liquid curing type urethane based dry laminate. In a case where polyester is used to form the tray 21, it is possible to preferably use the olefin resin such as ethylene-vinyl acetate resin and the ethylene-acrylic acid resin, a copolyester adhesive agent, and the adhesive agent consisting of the two-liquid curing type urethane based dry laminate.

It is preferable to form the surface protection layer by coating the upper surface of the hardly oxygen-permeable film with polyester, polypropylene, polyethylene, nylon, PET, epoxy resin or polyamide resin or by pasting films made of synthetic resin, paper, and the like together. The surface protection layer can be used as a printing layer to write necessary items such as the name of a medicine filled in the syringe 3 to be housed inside the tray, a filled content, and the like thereon. A light-shielding material such as white ink may be interposed between the surface protection layer and the hardly oxygen-permeable film to form a light-shielding film. It is conceivable to form the sealing sheet 25 of four layers of polyethylene terephthalate/ethylene-vinyl alcohol copolymer/drawn nylon/adhesive resin (hardly oxygen-permeable film is used) and of three layers of polyethylene terephthalate/drawn nylon/adhesive resin.

As concrete examples of the sealing sheet 25, it is conceivable to form the sealing sheet of four layers of polyethylene terephthalate/polyethylene/polyethylene terephthalate/adhesive resin, of four layers of polyethylene terephthalate/ethylene-vinyl alcohol copolymer/drawn nylon/adhesive resin, and of three layers of polyethylene terephthalate/drawn nylon/adhesive resin.

The oxygen scavenger is housed inside the packaging body 2. In the packaged medicine-filled container of this embodiment, both the moisture-dependent type oxygen scavenger 4 and the self-reacting type oxygen scavenger 5 are housed inside the tray 21. More specifically, both the moisture-dependent type oxygen scavenger 4 and the self-reacting type oxygen scavenger 5 are housed at a bottom part of the tray 21. In this embodiment, one (for example, moisture-dependent type oxygen scavenger 4) of the oxygen scavengers is housed inside the housing portion 23a for housing the front end portion of the outer cylinder, whereas the other (for example self-reacting type oxygen scavenger 5) of the oxygen scavengers is housed inside the plunger housing portion 23d with the two oxygen scavengers being spaced apart from each other. Although it is preferable to dispose the moisture-dependent type oxygen scavenger 4 and the self-reacting type oxygen scavenger 5 by spacing them apart from each other, they may be disposed closely.

It is preferable to unmovably house the moisture-dependent type oxygen scavenger 4 and the self-reacting type oxygen scavenger 5 inside the tray 21. As a method of preventing both oxygen scavengers from moving, it is conceivable to fix lower surfaces of the moisture-dependent type oxygen scavenger 4 and the self-reacting type oxygen scavenger 5 to a bottom surface of the tray 21. The moisture-dependent type oxygen scavenger 4 and the self-reacting type oxygen scavenger 5 may be fixed to a lower surface (inner surface) of the sealing sheet 25. Although it is preferable that the moisture-dependent type oxygen scavenger 4 and the self-reacting type oxygen scavenger 5 are separately housed inside the tray, both the moisture-dependent type oxygen scavenger 4 and the self-reacting type oxygen scavenger 5 may be filled inside one oxygen scavenger.

In this embodiment, the tray is used as the packaging body. The tray has a container body housing space, having a certain degree of capacity, which is formed in advance. Thus the sealed packaging body has a space having a certain degree of capacity and air filled inside the space. Because the moisture-dependent type oxygen scavenger having a high deoxygenation capability is used as the oxygen scavenger, the moisture-dependent type oxygen scavenger is capable of quickly removing oxygen contained in the air inside the packaging body in an early period of time together with moisture contained inside the packaging body. In a state where the inside of the packaging body has a low-moisture state and the moisture-dependent type oxygen scavenger does not display its deoxygenation function, the self-reacting type oxygen scavenger continuously absorbs the oxygen inside the packaging body. Thereby the packaged medicine-filled container is capable of continuously keeping the atmosphere inside the packaging body in a low-oxygen state.

As the moisture-dependent type oxygen scavenger, an iron-based moisture-dependent type oxygen scavenger is preferable. More specifically, the iron-based moisture-dependent type oxygen scavenger is described in Japanese Examined Patent Publication No. 56-33980. The composition of the oxygen scavenger has the structure in which metal powder of iron powder and the like is coated with the metal halide. As the moisture-dependent type oxygen scavenger, it is possible to exemplify AGELESS (registered trademark) produced by Mitsubishi Gas Chemical Company, Inc.

In the self-reacting type oxygen scavenger described in Japanese Examined Patent Publication No. 57-31449, the moisture donor is present in the oxygen scavenger so that the moisture donor supplies moisture necessary for deoxygenation to the atmosphere inside the container body housing space. As the self-reacting type oxygen scavenger having the moisture donor, it is possible to exemplify AGELESS (registered trademark) S type (S, SP, SS) which is the iron-based self-reacting type oxygen scavenger produced by Mitsubishi Gas Chemical Company, Inc.

As the self-reacting type oxygen scavenger, a type displaying a deoxygenation function in a dry atmosphere without the need of the moisture donor may be used. Examples of the self-reacting type oxygen scavenger of this type include the oxygen scavenger having the deoxidizing component consisting of the crosslinked macromolecules having carbon-carbon unsaturated bonds (for example, see Japanese Patent Application Laid-Open Publication No. 11-70331), the oxygen scavenger containing the activated metal as its main agent with the transition metal being carried by the carrier (for example, see Japanese Patent Application Laid-Open Publication No. 8-38883), the oxygen scavenger containing the activated magnesium obtained by reducing the magnesium compound after it is carried on the carrier as its main agent (for example, see Japanese Patent Application Laid-Open Publication No. 2001-37457), the oxygen scavenger having the oxygen absorption composition containing the liquid hydrocarbon having the unsaturated group as its main agent with the oxygen absorption accelerating substance being carried on the carrier (for example, see Japanese Patent Application Laid-Open Publication No. 10-113555), and the oxygen scavenger using the polyphenol compound as the oxidizable organic matter (see Japanese Patent Application Laid-Open Publication No. 2011-195185). As the oxygen scavenger of this type, it is possible to exemplify AGELESS (registered trademark) GLS, GP which are non-ferrous oxygen scavengers produced by Mitsubishi Gas Chemical Company, Inc.

In the embodiment of the present invention, the prefilled syringe is used as the medicine-filled container body. Examples of medicines to be housed inside the prefilled syringe include liquid medicines such as saline, a high-concentration sodium chloride injection solution, vitamin preparations, mineral agents, antibiotics; and powdery or freeze-dried medicine.

The packaged medicine-filled container of the present invention is especially effective for medicines which may decompose, undergo chemical associations, generate dimmers, color, precipitate, denature, be modified or lower in the contents thereof in the presence of oxygen.

Figure 2:
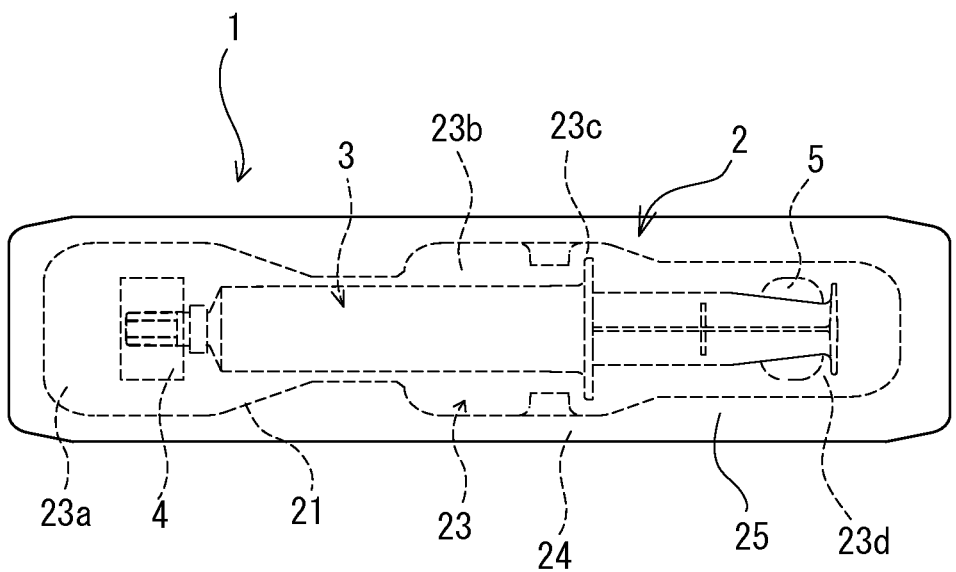
FIG. 2 is a plan view of the packaged medicine-filled container shown in FIG. 1.
Figure 3:
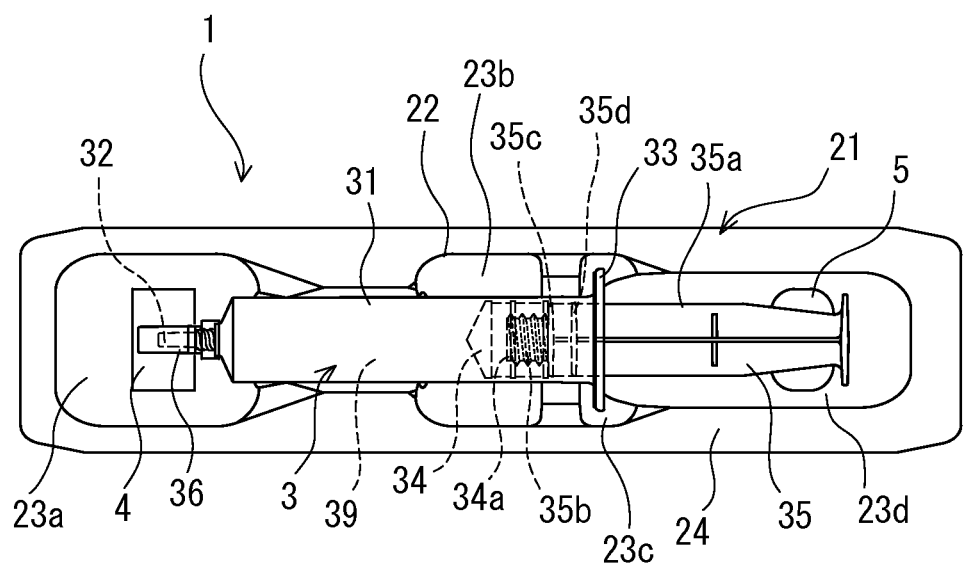
FIG. 3 is a plan view of a state in which a sealing sheet has been removed from the packaged medicine-filled container shown in FIG. 1.
Figure 4:
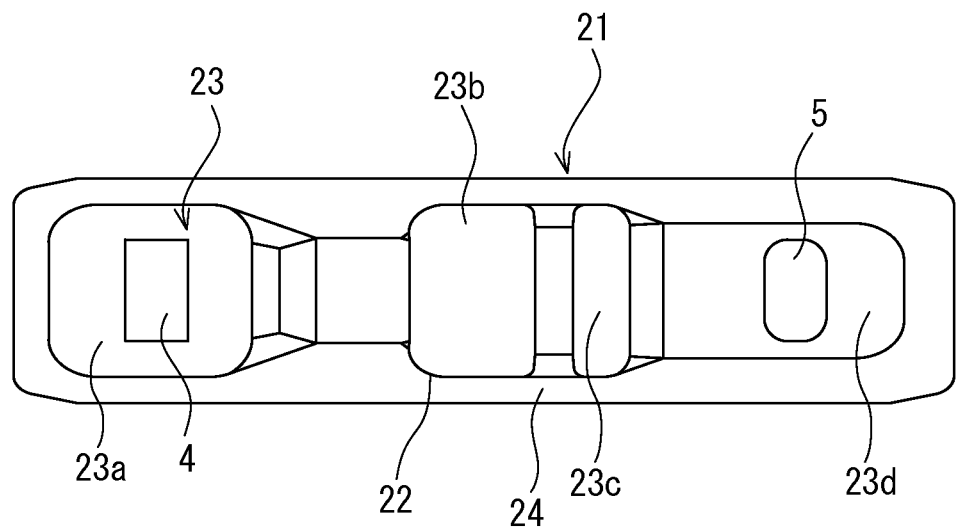
FIG. 4 is a plan view of a tray used for the packaged medicine-filled container shown in FIG. 1.

As shown in FIGS. 1 through 3, the prefilled syringe 3 to be used in the embodiment of the present invention has the outer cylinder 31 having a nozzle 32 disposed at its front end portion and a flange 33 at its rear end portion, a gasket 34 slidable inside the outer cylinder, a plunger 35 mounted on the gasket 34, a sealing member (more specifically, sealing cap mounted on the front end portion of the outer cylinder 31) 36 for sealing a front end portion of the outer cylinder 31, and the medicine 39 housed in the outer cylinder 31. An outer cylinder side threadedly engaging portion which threadedly engages a cap side threadedly engaging portion formed on the sealing cap 36 is formed at a proximal end portion of the nozzle. An outer cylinder side engaging portion which engages a cap side engaging portion formed on the sealing cap 36 is formed in the vicinity of the front end portion of an outer cylinder body.

An insertion needle can be inserted through the sealing cap 36. The sealing cap is composed of a sealing cap body and a sealing member. The sealing cap body is a tubular member open at its one and other ends. The opening at one end of the sealing cap body is closed with the sealing member. The sealing cap body is formed in the shape of a cap and has a nozzle body housing portion, the cap side threadedly engaging portion, and the sealing cap side engaging portion. The sealing member has a function of liquid-tightly sealing the opening at the front end of the nozzle part. The nozzle part is liquid-tightly sealed by contact between the opening at the front end of the nozzle part and the sealing member.

The sealing member is formed of an elastic material through which a liquid-passing needle can be pierced. The sealing member has the function of liquid-tightly sealing the opening at the front end of the nozzle part. The sealing member is formed of an elastic material through which the liquid-passing needle can be pierced. The sealing member is mounted on a front end portion of the cap 36 by means of a sealing member holding portion.

It is preferable to use natural rubber, synthetic rubber such as isoprene rubber, butadiene rubber, fluororubber, and silicone rubber; and thermoplastic elastomers including styrene elastomers such as SBS elastomer and SEBS elastomer; and polyolefin elastomers such as ethylene-α-olefin copolymer as materials for forming the sealing member.

As shown in FIG. 3, the plunger 35 is composed of a body part 35a cross-shaped in its section and a threadedly engaging portion 35b which threadedly engages the gasket 34 provided at a front end portion of the body part 35a. Disk-shaped ribs 35c and 35d are formed at the front end portion of the body part 35a. A rib is formed in the vicinity of a center of the body part 35a.

As shown in FIG. 3, a threadedly engaging concave portion 34a which threadedly engages the threadedly engaging portion 35b formed at the front end portion of the plunger 35 is formed inside the gasket 34. In this embodiment, the diameter of the gasket 34 increases in the vicinity of its front end portion and proximal end portion. Thus the gasket is in contact with the inner surface of the outer cylinder at these portions. In the gasket of this embodiment of the present invention, a rib is formed in the vicinity of its front end portion, central portion, and proximal end portion. Thus the gasket is in contact with the inner surface of the outer cylinder at these portions.

As materials for forming the outer cylinder 31, materials transparent or semitransparent are used. It is preferable to use materials having a low degree of water vapor permeability to prevent water evaporation of the liquid medicine housed in the prefilled syringe. As materials for forming the outer cylinder 31, it is possible to list various resins including polyester such as polypropylene, polyethylene, polystyrene, polyamide, polycarbonate, polyvinyl chloride, poly-(4-methylpentene-1), acrylic resin, an acrylonitrile-butadiene-styrene copolymer, and polyethylene terephthalate; and cyclic polyolefin. Of these resins, the polypropylene and the cyclic polyolefin are preferable because these resins are easily moldable and heat-resistant. The cyclic polyolefin is especially preferable because the cyclic polyolefin has a low degree of water vapor permeability.

As materials for forming the sealing cap 36, it is preferable to use materials having a low degree of water vapor permeability. As the material for forming the sealing cap 36, it is possible to list various resins such as polyester including polypropylene, polyethylene, polystyrene, polyamide, polycarbonate, polyvinyl chloride, poly-(4-methylpentene-1), acrylic resin, an acrylonitrile-butadiene-styrene copolymer, and polyethylene terephthalate; and cyclic polyolefin. Of these resins, the polypropylene and the cyclic polyolefin are preferable because these resins are easily moldable and heat-resistant.

As materials for forming the gasket 34, it is preferable to use elastic rubber (for example, butyl rubber, latex rubber, silicone rubber) and synthetic resin (for example, styrene elastomers such as SBS elastomer, SEBS elastomer; and olefin elastomers such as ethylene-α-olefin copolymer). In the present invention, known prefilled syringes are used. As the materials for the gasket 34, it is preferable to use elastic materials having a low degree of water vapor permeability. More specifically, the butyl rubber is preferable.

It is preferable that the medicine-filled container to be used in the embodiment of the present invention has entirely a low degree of water vapor permeability. As described above, it is preferable that the outer cylinder 31 is formed of a hardly water vapor-permeable material. It is also preferable that water vapor is permeable to a low extent at a contact portion between the gasket and the outer cylinder.

The prefilled syringe has the outer cylinder formed of resin having a low degree of water vapor permeability, the gasket slidable inside the outer cylinder and formed of an elastic material having a low degree of water vapor permeability, the sealing member mounted on the front end portion of the outer cylinder. It is preferable that the medicine is housed inside the outer cylinder. More specifically, it is preferable to combine the outer cylinder formed of the cyclic polyolefin with the gasket formed of the butyl rubber. As described above, it is preferable that the medicine-filled container has a low degree of water vapor permeability in terms of "permeability". Further the medicine-filled container of the present invention is particularly effective in a case where oxygen permeates through any of parts (outer cylinder, gasket, sealing member) thereof.

The medicine-filled container of the present invention is not limited to the above-described prefilled syringe, but may be a medicine-filled ample made of resin, a medicine-filled vial container made of resin, an ample, and a liquid medicine-filled infusion container.

The packaging body is not limited to the above-described one having the tray. The packaging body may have the shape of a hardly oxygen-permeable bag. It is conceivable that the bag-shaped packaging body can be formed by superimposing sealing sheets on each other and sealing peripheral portions thereof. In a case where the packaging body of this type is used, it is preferable to fix the oxygen scavenger for the oxygen scavenger to be housed inside the packaging body to the inner surface of the packaging body.

Figure 5:
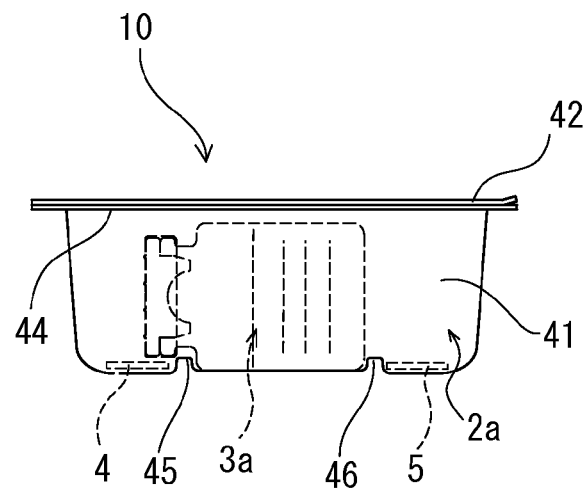
FIG. 5 is a front view of a packaged medicine-filled container which is another embodiment of the present invention.
Figure 6:
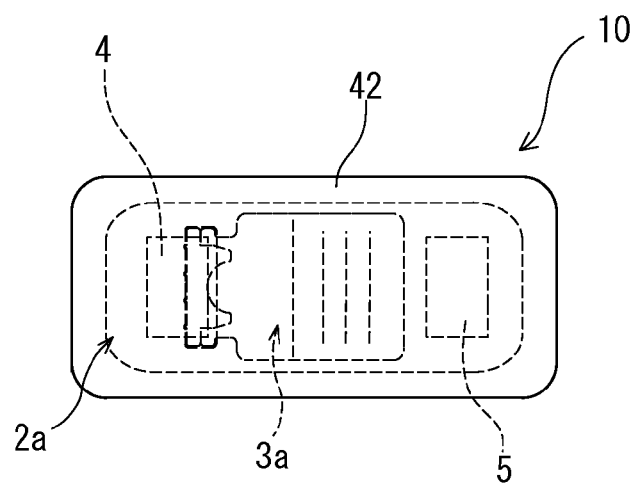
FIG. 6 is a plan view of the packaged medicine-filled container shown in FIG. 5.
Figure 7:
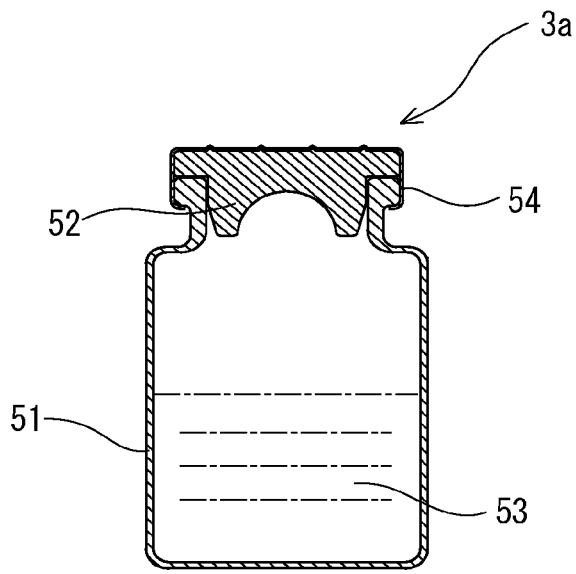
FIG. 7 is a sectional view of a resin-made medicine-filled container for use in the packaged medicine-filled container shown in FIG. 5.

A so-called vial container 3a like a medicine-filled container 10 as shown in FIGS. 5 through 7 may be used as the packaged medicine-filled container of the present invention.

A packaged medicine-filled container 10 of this embodiment is constructed of a resin-made medicine-filled container 3a composed of a resin-made container main body 51 in which a medicine 53 is housed and a sealing member 52 mounted on an open part of the container main body 51 and a sealed packaging body 2a in which the medicine-filled container 3a is housed. The packaged medicine-filled container 10 has an oxygen scavenger housed inside the packaging body 2a thereof. The packaging body 2a is hardly oxygen-permeable. As the oxygen scavenger, both the moisture-dependent type oxygen scavenger 4 and the self-reacting type oxygen scavenger 5 are used. As the moisture-dependent type oxygen scavenger 4 and the self-reacting type oxygen scavenger 5, the above-described ones are used.

In the packaged medicine-filled container 10 of this embodiment, as the medicine-filled container 3a, a vial container in which a liquid medicine is filled as the medicine 53 is used. The packaging body 2a to be used in this embodiment has a tray 41 where the vial container which is the medicine-filled container 3a is housed and a sealing member 42 for openably sealing an opening of the tray 41. The tray 41 has a container body housing part and a flange-formed part 44 formed around an upper edge of the container body housing part. The tray 41 has projected portions 45 and 46 disposed on a bottom surface of the container body housing part to prevent a movement of the container 3a. The material for forming the tray and the construction thereof are the same as those of the above-described tray 21. The material and construction of the sealing member 42 are also the same as those of the above-described sealing member 25.

In the present invention, the resin-made container main body 51 which has the open part and is capable of housing a medicine inside is used. As materials for forming the resin-made container main body 51, a container made of hard or semi-hard synthetic resin is used. The resin-made container main body 51 shown in the drawings has a cylindrical body part whose lower end is closed, the open part having a thick flange, and a neck part, having a diameter smaller than those of the other parts, which are formed between the open part and the body part. A part of the resin-made container main body 51 disposed from its open part to neck part is formed as a housing part for housing an entry portion, of the sealing member 52, which is inserted into the container. The sealing member 52 extends in the same inner diameter in the range from the open part to the neck part.

As hard or semi-hard synthetic resin to be used to form the resin-made container main body 51, it is preferable to use general-purpose various hard plastic materials including polyolefin such as polypropylene, polyethylene, poly(4-methylpentene-1), and cyclic polyolefin; polyester such as polyethylene terephthalate, polyethylene naphthalate, and amorphous polyarylate; polystyrene; polyamide; polycarbonate; polyvinyl chloride; acrylic resin; an acrylonitrile-butadiene-styrene copolymer, and amorphous polyetherimide. The polypropylene, the poly(4-methylpentene-1), the cyclic polyolefin, polyethylene naphthalate, and the amorphous polyetherimide are preferable in terms of the transparency and heat sterilization resistance thereof. The acyclic polyolefin is especially preferable because it has a low degree of water vapor permeability and many advantages.

A rubber stopper is suitable as the sealing member 52. The rubber stopper 52 shown in the drawings has a disk-shaped body part and the entry portion which extends downward in an outer diameter smaller than that of the body part from the center of a lower surface of the body part. The configuration of the rubber stopper is merely an example and may have any configurations so long as the rubber stopper is capable of liquid-tightly sealing the open part of the medicine container. Although the above-described rubber stopper has the entry portion, the rubber stopper may have a tubular part encapsulating the outer side of the open part of the resin-made container main body 51 instead of the entry portion.

As materials for composing the rubber stopper, elastic materials are preferable. Although the elastic materials are not specifically limited to particular ones, it is possible to use various rubber materials (materials subjected to vulcanization treatment are especially preferable) such as natural rubber, isoprene rubber, butyl rubber, chloroprene rubber, nitrile-butadiene rubber, styrene-butadiene rubber, and silicone rubber. Dine rubber is especially preferable because it has an elastic property and can be subjected to γ-ray sterilization, electron beam sterilization, and high-pressure steam sterilization. As materials for forming the rubber stopper, elastic materials having a low degree of water vapor permeability is preferable. More specifically, the butyl rubber is preferable. Therefore in the packaged medicine-filled container 10 of the type of this embodiment, it is preferable to combine the resin-made container main body 51 formed of the cyclic polyolefin with the rubber stopper which is the sealing member formed of the butyl rubber.

The medicine-filled container 3a shown in the drawings has an encapsulating member 54 for encapsulating a peripheral portion of the open part of the container main body 51 on which the rubber stopper has been mounted and a peripheral portion of the rubber stopper 52. It is preferable that the encapsulating member 54 is formed of an aluminum film or a heat-shrinkable film and closely contacts the rubber stopper and the medicine container main body. The encapsulating member 54 may cover the entire upper surface of the rubber stopper, provided that a piercing needle such as an injection needle can be pierced thereinto. In this case, it is preferable to use the encapsulating member 54 having a low degree of water vapor permeability (for example, aluminum film, hardly water vapor-permeable resin film). In a case where the encapsulating member 54 is hardly water vapor-permeable, the rubber stopper 52 does not necessarily have to be hardly water vapor-permeable. The pressure of the inside of the medicine-filled container 3a may be reduced.

Figure 8:
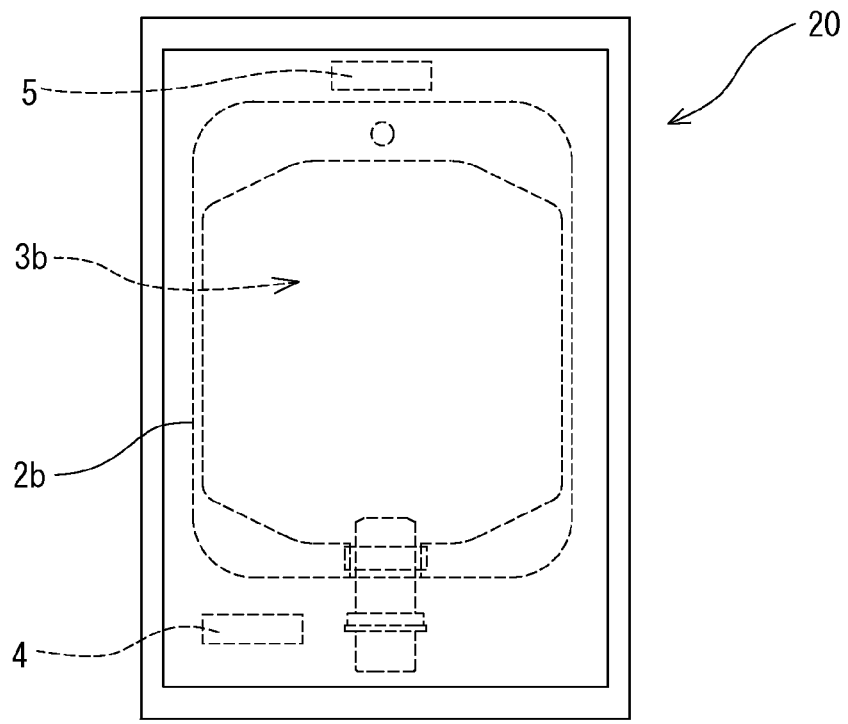
FIG. 8 is a front view of a packaged medicine-filled container which is still another embodiment of the present invention.
Figure 9:
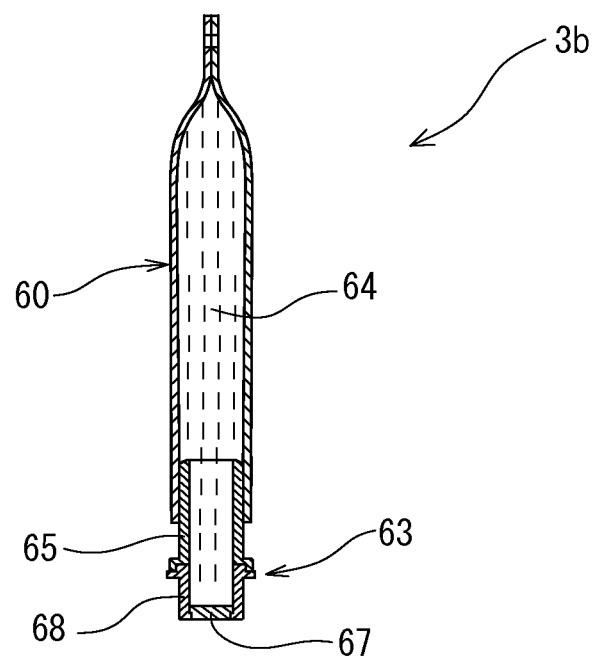
FIG. 9 is a sectional view of a resin-made medicine-filled container for use in the packaged medicine-filled container shown in FIG. 8.

A so-called soft bag 60 like a medicine-filled container as shown in FIGS. 8 and 9 may be used as the packaged medicine-filled container of the present invention.

A packaged medicine-filled container 20 of this embodiment is composed of a medicine-filled container 3b in which a medicine (liquid medicine) 64 is housed and a sealed packaging body 2b in which the medicine-filled container 3b is housed. The packaged medicine-filled container 20 has an oxygen scavenger housed inside the packaging body 2b. The packaging body 2b is hardly oxygen-permeable. Both the moisture-dependent type oxygen scavenger 4 and the self-reacting type oxygen scavenger 5 are used as the oxygen scavenger. As the moisture-dependent type oxygen scavenger 4 and the self-reacting type oxygen scavenger 5, the above-described ones are used.

The medicine-filled container 3b is used for the packaged medicine-filled container 20 of this embodiment. As the medicine, a liquid medicine 64 is used. The resin-made soft bag 60 is used as a resin-made container main body. A discharge port 63 is mounted on the resin-made soft bag 60. In this embodiment, the discharge port 63 has a synthetic resin-made discharge port main body 65 and a discharge outlet having an elastic sealing member 67, for closing an end portion of the discharge port body 65, which is connectable to a piercing needle pierced therethrough. The discharge outlet has a cap 68 for housing the elastic sealing member 67.

The soft bag 60 is formed of soft synthetic resin. It is preferable to form the soft bag in a tubular configuration by using an inflation molding method. The soft bag 60 may be produced by using a blow molding method, a co-extrusion inflation method or the like.

As materials for forming the soft bag 60, it is possible to list various materials polyolefin such as polyethylene (PE), polypropylene (PP), polybutadiene, and cyclic polyolefin; thermoplastic elastomers such as olefin elastomers, and styrene elastomers or arbitrarily selected combinations (blend resin, polymer alloy, laminate, and the like) of the above materials. It is preferable that resin materials to be used for the soft bag have heat resistance and pressure resistance to such an extent as to withstand against high pressure steam sterilization (autoclave sterilization). The cyclic polyolefin having a low degree of water vapor permeability is especially preferable. As sheet materials for forming the soft bag 60, of the above-described materials of the sealing sheet (sealing member) 25, those hardly water vapor-permeable may be used.

As materials for forming the discharge port main body and the cap, it is possible to use polyolefins such as polyethylene, polypropylene, cyclic polyolefin, and an ethylene-propylene copolymer; polyesters such as polyethylene terephthalate and polybutylene terephthalate; styrene resins such as polystyrene, MS resin (methacrylate-styrene copolymer), MBS resin (methacrylate-butylene-styrene copolymer); polyvinyl chloride, polyamide such as 6 nylon, 66 nylon, and the like. The cyclic polyolefin is especially preferable because it has a low degree of water vapor permeability and many advantages.

As materials for constructing the elastic sealing member 67, elastic materials are preferable. Although the elastic materials are not specifically limited to particular ones, it is possible to use various rubber materials (materials subjected to vulcanization treatment are especially preferable) such as natural rubber, isoprene rubber, butyl rubber, chloroprene rubber, nitrile-butadiene rubber, styrene-butadiene rubber, and silicone rubber. Dine rubber is especially preferable because it has an elastic property and can be subjected to γ-ray sterilization, electron beam sterilization, and high-pressure steam sterilization. As materials for forming the elastic sealing member 67, elastic materials having a low degree of water vapor permeability is preferable. More specifically, the butyl rubber is preferable. A hardly water vapor-permeable film may be stuck to an upper surface of the discharge port 63 in such a way as to encapsulate the elastic sealing member 67. In this case, the material for the elastic sealing member 67 does not necessarily have to be hardly water vapor-permeable.

It is preferable to fix the moisture-dependent type oxygen scavenger 4 and the self-reacting type oxygen scavenger 5 to an inner surface of the packaging body 2b.

As the packaging body 2b, a bag-shaped packaging body having a housing space which is capable of housing the medicine-filled container 3b therein and is flexible is used. After the medicine-filled container 3b is housed inside the packaging body 2b, the open part of the packaging body 2b is heat-sealed to bring the packaging body into a sealed state. The sealed packaging body 2b consisting of a hardly gas-permeable film is used. It is preferable that the film is light-shieldable. More specifically, it is preferable that the packaging body is made of a film which has an aluminum-deposited layer, an aluminum-foil layer or a silica ($SiO_2$)-deposited layer and is light-shieldable and hardly gas-permeable. It is especially preferable to use a laminated film consisting of the aluminum-deposited layer or the aluminum foil layer sandwiched between hardly gas-permeable films consisting of a polymeric material. As hardly gas-permeable polymeric materials for forming a hardly gas-permeable laminated film, it is possible to list polyester such as biaxially oriented polyamide, an ethylene-vinyl alcohol copolymer, and polyethylene terephthalate; and polyvinylidene chloride.

In the case of the laminated film, it is preferable to compose an intermediate layer of the aluminum-deposited layer or the aluminum foil layer. The laminated film can be formed by fusion-bonding one or two layers consisting of the hardly gas-permeable polymeric material to the aluminum-deposited layer or the aluminum foil layer by using an adhesive agent layer (for example, polyethylene, ethylene-vinyl acetate copolymer) consisting of resin having a low melting point. It is preferable to form a resin layer having a low melting point on an inner surface of the laminated film to seal the packaging body therewith. Although the resin layer having a low melting point may be formed on the entire inner surface of the film, it may be formed on only a portion to be heat-sealed or in the vicinity thereof. As materials for forming the resin layer having a low melting point, so-called hot melt materials are used. More specifically, the low melting point resin such as polyethylene (for example, low molecular weight polyethylene) or an ethylene-vinyl acetate copolymer is used.

INDUSTRIAL APPLICABILITY

The packaged medicine-filled container of the present invention has the form as described below.

(1) A packaged medicine-filled container comprising a resin-made medicine-filled container in which a medicine is housed and a sealed packaging body in which said medicine-filled container is housed, wherein said packaged medicine-filled container has an oxygen scavenger housed inside said packaging body; said packaging body is hardly oxygen-permeable; and both a moisture-dependent type oxygen scavenger and a self-reacting type oxygen scavenger are used as said oxygen scavenger.

By using the moisture-dependent type oxygen scavenger as the oxygen scavenger, it is possible to quickly remove oxygen contained in the air inside the packaging body in an early period time together with moisture contained inside the packaging body, even though the packaging body has a certain degree of volume. In a state where the inside of the packaging body a low moisture state and thus the moisture-dependent type oxygen scavenger does not display a deoxygenation function, the self-reacting type oxygen scavenger absorbs the oxygen inside the packaging body continuously. Thereby it is possible to keep the inside of the packaging body in a low-oxygen state. When the inside of the packaging body has low oxygen and humidity states owing to the action of the oxygen scavengers, there is a possibility that oxygen permeates into the packaging body owing to factors such as an environmental change. As described above, because the self-reacting type oxygen scavenger is used for the packaged medicine-filled container of the present invention, the packaged medicine-filled container is capable of coping with the permeation of oxygen into the packaging body.

The above-described embodiments may have the following forms.

(2) A packaged medicine-filled container according to the above (1), wherein said resin-made medicine-filled container is a prefilled syringe in which a liquid medicine is filled as said medicine.

(3) A packaged medicine-filled container according to the above (2), wherein said prefilled syringe comprises an outer cylinder formed of resin having a low degree of water vapor permeability; a gasket which is slidable inside said outer cylinder and formed of an elastic material having a low degree of water vapor permeability; a sealing member for sealing a front end portion of said outer cylinder; and said medicine housed inside said outer cylinder.

(4) A packaged medicine-filled container according to any one of the above (1) through (3), wherein said moisture-dependent type oxygen scavenger is an iron-based moisture-dependent type oxygen scavenger.

(5) A packaged medicine-filled container according to any one of the above (1) through (4), wherein said self-reacting type oxygen scavenger is an iron-based self-reacting type oxygen scavenger or an organic self-reacting type oxygen scavenger.

(6) A packaged medicine-filled container according to any one of the above (1) through (5), wherein said packaging body has a tray having an opening and a container body housing part and a sealing sheet for sealing said opening of said tray.

(7) A packaged medicine-filled container according to any one of the above (1) through (6), wherein said resin-made medicine-filled container has a low degree of water vapor permeability.

(8) A packaged medicine-filled container according to the above (7), wherein said resin-made medicine-filled container has a container main body which is formed of resin having a low degree of water vapor permeability and has an open part and a sealing member which seals said open part of said container main body and is formed on an elastic material having a low degree of water vapor permeability.

The invention claimed is:
1. A composition comprising:
a prefilled syringe comprising:
an outer cylinder formed of polypropylene or cyclic polyolefin, the outer cylinder comprising a nozzle,
a medicine housed in said outer cylinder,
a gasket housed in said outer cylinder and slidable inside said outer cylinder, said gasket being formed of butyl rubber, and
a sealing member for sealing said nozzle of said outer cylinder, the sealing member being formed of a material low water vapor permeability;

a sealed packaging body in which said prefilled syringe is housed, wherein said packaging body has low oxygen permeability;

a moisture-dependent type oxygen scavenger housed inside said packaging body; and a self-reacting type oxygen scavenger housed inside said packaging body.

2. The composition according to claim 1, wherein said moisture-dependent type oxygen scavenger is an iron-based moisture-dependent type oxygen scavenger.

3. The composition according to claim 1, wherein said self-reacting type oxygen scavenger is an iron-based self-reacting type oxygen scavenger or an organic self-reacting type oxygen scavenger.

4. The composition according to claim 1, wherein said packaging body comprises:

a tray having an opening and comprising a syringe housing part, and a sealing sheet sealing said opening of said tray.

5. The composition according to claim 4, wherein:

said moisture-dependent type oxygen scavenger and said self-reacting type oxygen scavenger are fixed to a bottom of said tray inside said tray.

6. The composition according to claim 5, wherein:

said tray has a first side and a second side, said second side being opposite said first side in a longitudinal direction of said tray; and said moisture-dependent type oxygen scavenger is fixed to said bottom of said tray at said first side of said tray, and said self-reacting type oxygen scavenger is fixed to said bottom of said tray at said second side of said tray.

7. The composition according to claim 1, wherein said outer cylinder is formed of cyclic polyolefin.

* * * * *